(12) United States Patent
Bosman et al.

(10) Patent No.: US 8,876,760 B2
(45) Date of Patent: Nov. 4, 2014

(54) PISTON PUMP WITH VARIABLE BUFFER

(75) Inventors: Franciscus Jozef Bosman, Eindhoven (NL); Johannes Willem Tack, Eindhoven (NL); Egbert Van De Veen, Eindhoven (NL); Pieter Bax, Eindhoven (NL); Bernardo Arnoldus Mulder, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/810,866

(22) PCT Filed: Jul. 22, 2011

(86) PCT No.: PCT/IB2011/053277
§ 371 (c)(1),
(2), (4) Date: Jan. 17, 2013

(87) PCT Pub. No.: WO2012/014135
PCT Pub. Date: Feb. 2, 2012

(65) Prior Publication Data
US 2013/0123689 A1    May 16, 2013

(30) Foreign Application Priority Data
Jul. 29, 2010   (EP) ..................................... 10171248

(51) Int. Cl.
*A61M 1/06*   (2006.01)
*A61M 1/16*   (2006.01)

(52) U.S. Cl.
CPC ............... *A61M 1/06* (2013.01); *A61M 1/1698* (2013.01)
USPC ........................................................... 604/74

(58) Field of Classification Search
USPC .................................................. 604/74, 119
See application file for complete search history.

(56) References Cited

U.S. PATENT DOCUMENTS

| | | | |
|---|---|---|---|
| 5,007,899 A * | 4/1991 | Larsson ........................ | 604/74 |
| 6,673,036 B1 | 1/2004 | Britto et al. | |
| 2001/0038799 A1 * | 11/2001 | Silver et al. .................... | 417/515 |
| 2004/0215138 A1 | 10/2004 | Greter et al. | |
| 2005/0043677 A1 | 2/2005 | Kelly et al. | |
| 2008/0009815 A1 | 1/2008 | Grabenkort et al. | |
| 2009/0099511 A1 * | 4/2009 | Sutrina et al. .................. | 604/74 |

FOREIGN PATENT DOCUMENTS

| | | |
|---|---|---|
| WO | 0066195 A1 | 5/2000 |
| WO | 2005067997 A1 | 7/2005 |

* cited by examiner

*Primary Examiner* — Nicholas Lucchesi
*Assistant Examiner* — Diva K Chander

(57) ABSTRACT

A breast pump apparatus, including a vacuum pump and a variable-volume buffer volume coupled together in fluid communication, also includes a breast-receiving portion coupled to the vacuum pump and the buffer volume such that the vacuum pump is operable to generate negative pressure at the breast-receiving portion to stimulate milk expression, and the negative pressure generated at the breast-receiving portion can be controlled by controlling the buffer volume.

15 Claims, 5 Drawing Sheets

PISTON PUMP WITH VARIABLE BUFFER

FIELD OF THE INVENTION

The present invention relates to a pump apparatus for use in a breast pump device used for expressing milk from a mother's breast and, more particularly, to a pump apparatus that includes a variable buffer volume.

BACKGROUND OF THE INVENTION

Breast pumps are devices which are designed to express milk from a mother's breast to a storage container, such as a feeding bottle to enable the mother to feed the breast milk to the baby at a later or more convenient time. Breast pumps generally comprise a funnel portion to receive the woman's breast, and a vacuum chamber coupled to each other, and a vacuum pump operable to repeatedly generate reduced pressure in the vacuum chamber, and thereby create a reduced pressure in the funnel, to stimulate the woman's breast to express milk into the funnel to be collected in the storage container connected to the vacuum chamber/funnel. In such breast pump devices, the vacuum pump can typically comprise a reciprocating piston or a reciprocating resilient membrane.

A breast pump device comprising a reciprocating resilient membrane for generating a vacuum is known from US 2001/038799, for example. US 2009/099511 discloses the use of a pump mechanism having a manually operable handle for effecting the vacuum. Both breast pump devices known from US 2001/038799 and US 2009/099511 include a mechanism to regulate vacuum within the funnel of the device, particularly minimum and maximum levels of the vacuum, wherein the mechanism comprises a valve-like construction for performing a sealing function in one position, and allowing air to escape in another position.

WO 2005/067997 also discloses the use of a pump mechanism having a handle for effecting the vacuum, wherein the handle is connected to a piston which is adapted to perform a reciprocating movement inside the breast pump device. In the funnel of the device, flexible membranes are arranged, which inflate during operation to massage the breast which is present inside the funnel.

Known breast pumps can include control means to enable the pressure depth generated by the vacuum pump within the vacuum chamber, and thereby at the breast funnel, to be regulated. Such known control means comprise varying the stroke of the reciprocating piston/resilient membrane, requiring the motor that drives the piston/resilient membrane and the transmission between the motor and the piston/resilient membrane to be able to operate in a reciprocating manner—namely to operate in two directions to enable the stroke of the reciprocating movement of the piston/resilient membrane to be varied. The construction of such a mechanism which includes a motor and transmission configured to operate in two directions in a reciprocating manner, as well as a motor control system to control such a configuration of mechanism, is complex and therefore results in a relatively high cost of manufacture. Furthermore, the reciprocating movement of the motor and transmission is not very energy efficient, leading to increased energy consumption, and such mechanisms can also lead to accelerated wear of the mechanical components. Yet further, motors which are capable of operating in two directions are more expensive than those which are capable of operating in only one single direction.

It would be advantageous to provide a pump apparatus suitable for use in a breast pump device which substantially alleviates or overcomes the problems mentioned above.

SUMMARY OF THE INVENTION

Accordingly, the present invention provides a breast pump apparatus comprising a vacuum pump operable to generate at least a negative pressure in a closed volume, a breast-receiving portion configured to receive a woman's breast from which milk is to be expressed and, a buffer volume, wherein the buffer volume is coupled to the vacuum pump and to the breast-receiving portion such that, in use, the vacuum pump is operable to generate at least a negative pressure in the buffer volume and at the breast-receiving portion, and wherein the buffer volume is variable such that, in use, the pressure depth at the breast-receiving portion generated by the vacuum pump, i.e. the amplitude of the negative pressure generated at the breast-receiving portion, can be controlled by controlling the buffer volume. With a breast pump apparatus of the invention, the magnitude of the pressure variations created by the pump and experienced at the breast can be controlled by varying the volume of the buffer volume. Therefore, the vacuum pump does not necessarily provide the pressure depth control, and so, if the vacuum pump is powered by a motor, the breast pump apparatus can comprise a uni-directional motor and transmission which is operable in a constant direction and continuously once in use, thereby avoiding the disadvantages of known systems described above.

The breast pump apparatus may further comprise a diaphragm chamber and a flexible diaphragm mounted within the diaphragm chamber, separating the diaphragm chamber into a closed side which is in fluid communication with the vacuum pump and the buffer volume, and an open side which is in fluid communication with the breast-receiving portion. In such an embodiment, the vacuum pump, the buffer volume and the closed side of the diaphragm chamber in fluid communication with each other could form a closed pneumatic system. Also in such an embodiment, the pressure variations generated in the closed side of the diaphragm chamber may cause the resilient diaphragm to deflect and thereby transmit the pressure variations to the open side of the diaphragm chamber and to the breast-receiving portion.

Alternatively, the breast-receiving portion, the buffer volume and the vacuum pump may be in fluid communication with each other. In such an embodiment, in use, when a mother's breast is received in the breast-receiving portion and an air-tight seal is made therewith, the vacuum pump, the buffer volume and the breast-receiving portion may together form a closed pneumatic system.

The pump may comprise a piston or may comprise a resilient membrane mounted within a housing. The pump is operable, upon drive from the motor, to generate negative pressure within the breast-receiving portion and/or closed pneumatic system. In the instance where the pump comprises a piston within a piston housing, the piston may be moveable, in use, over a constant, fixed stroke distance. The motor may be a DC motor, or an electronic commutated motor. Furthermore, the invention is not limited to the above type of vacuum pump, and many other known types of pump may be used, such as a manually operated pump (e.g. operated by a manually operated level or other actuator), a balloon pump, a gear pump, a bellows-type pump, a gerotor, a lobe pump or a resonant linear actuator pump.

The buffer volume may comprise a variable-volume chamber and the variable volume chamber may comprise a piston housing and a piston within the piston housing, and the volume of the buffer volume may be varied by moving the piston with the piston housing.

The pump may be configured to generate a substantially constant negative pressure, such pressure may be generated within the closed pneumatic system and, the piston of the buffer volume may be configured to reciprocate within the piston housing to cyclically vary the pressure at the breast-receiving portion and/or within the closed pneumatic system. Therefore, the movement of the piston may determine the pressure variation frequency at the breast-receiving portion and/or within the closed pneumatic system.

The piston of the buffer volume may be driven by a motor via a transmission, said transmission may comprise an eccentric/cam element, and the motor may be a unidirectional motor such that the piston may be moveable over a fixed stroke distance.

Alternatively, the variable volume chamber may comprise a housing having a moveable wall portion, and the volume of the buffer volume may be varied by moving the moveable wall portion relative to the housing.

The vacuum pump may be configured to cyclically generate varying negative pressure at the breast-receiving portion and/or within the closed pneumatic system and, the moveable wall of the variable volume chamber may be controllable to determine the amplitude of the negative pressure variations generated at the breast-receiving portion and/or within the closed pneumatic system. Therefore, the pump may control the pressure variation frequency within the closed pneumatic system.

The moveable wall portion may be moveable by means of a motor coupled to a piston by, for example, a cam or eccentric element. Alternatively, the motor may move the wall portion by means of another coupling configuration, such as a worm gear to transform rotational movement of the shaft of the motor to translational movement of the moveable wall.

The variable volume chamber of the buffer volume may include a first 'leakage' valve to allow ambient air into the variable volume chamber if the pressure therein falls below a predetermined negative pressure limit. Furthermore, the buffer volume may include an 'over-pressure' valve to allow air within the variable volume chamber to escape to atmosphere if the pressure therein rises above a predetermined upper pressure limit—that predetermined upper pressure limit may be atmospheric pressure.

As a further alternative, the buffer volume may comprise a plurality of fixed volume chambers, each in fluid communication with the vacuum pump and/or with the closed pneumatic system via a respective valve, and the volume of the buffer volume in fluid communication with the pump, and/or the volume of the closed pneumatic system, may be varied by selectively opening or closing each valve independently of each other valve so that the fixed volume chambers can selectively be closed off from, or in fluid communication with, the vacuum pump and/or closed pneumatic system.

Each of the fixed volume chambers may have a different volume to each of the other of the fixed volume chambers. The pump may be configured to cyclically generate varying negative pressure at the breast-receiving portion and/or within the closed pneumatic system and, the valves of the fixed volume chambers may be independently controllable to determine the amplitude of the negative pressure variations generated at the breast-receiving portion and/or within the closed pneumatic system.

The breast pump apparatus may further comprise a pressure sensor in fluid communication with the buffer volume and/or within the closed pneumatic system and, a controller coupled to the pressure sensor and to the buffer volume, and the volume of the buffer volume and/or the closed pneumatic system may be varied in dependence on a sensed pressure.

The breast pump apparatus may be configured such that the pressure variations experienced at the breast-receiving portion vary within the range of 0 mbar pressure to −330 mbar pressure, relative to atmospheric pressure. However, the invention is not limited to an apparatus configured to operate within this pressure range and many other pressure ranges are intended within the scope of the invention, such as a smaller or larger pressure range, a range varying between two negative pressures or, a pressure range varying between a negative pressure as a lower pressure range end value and a positive pressure—i.e. a pressure above atmospheric pressure—as an upper pressure range end value.

The vacuum pump may be driven by a motor which may be a uni-directional motor and the piston(s) of the vacuum pump and/or of the buffer volume may be configured to be operable over a constant stroke distance. The or each piston may be driven by a motor by a coupling to convert rotational movement of the motor shaft to translational movement of the piston. Such a coupling may comprise an eccentric/cam element. A reduction gearing may be provided in a transmission between the motor and the piston to reduce the speed of reciprocation of the piston relative to the speed of rotation of the motor shaft that is driving the piston.

The present invention also provides a method of controlling a breast pump apparatus as described above, the method comprising operating the vacuum pump to generate at least a negative pressure in the buffer volume and at the breast-receiving portion, and controlling the pressure depth at the breast-receiving portion, i.e. the amplitude of the negative pressure generated at the breast-receiving portion, by controlling the variable buffer volume. Varying the buffer volume may vary the total volume of the closed pneumatic system.

The buffer volume may comprise a variable-volume chamber and the pressure at the breast-receiving portion may be varied by controlling the volume of the variable-volume chamber. The total volume of the closed pneumatic system may be varied by controlling the volume of the variable volume chamber.

Alternatively, the buffer volume may comprise a plurality of fixed volume chambers in fluid communication with the vacuum pump and/or with the closed pneumatic system via a respective valve, and the method may further comprise varying the total volume of the buffer volume in fluid communication with the vacuum pump, and/or varying the volume of the closed pneumatic system, by selectively opening or closing each valve independently of each other valve so that each of the fixed volume chambers is selectively closed off from or in fluid communication with, the vacuum pump and/or the closed pneumatic system.

BRIEF DESCRIPTION OF THE DRAWINGS

Embodiments of the present invention will now be described, by way of example only, with reference to FIGS. 2-4 of the accompanying drawings, in which.

DETAILED DESCRIPTION OF THE EMBODIMENTS

Figure 1:
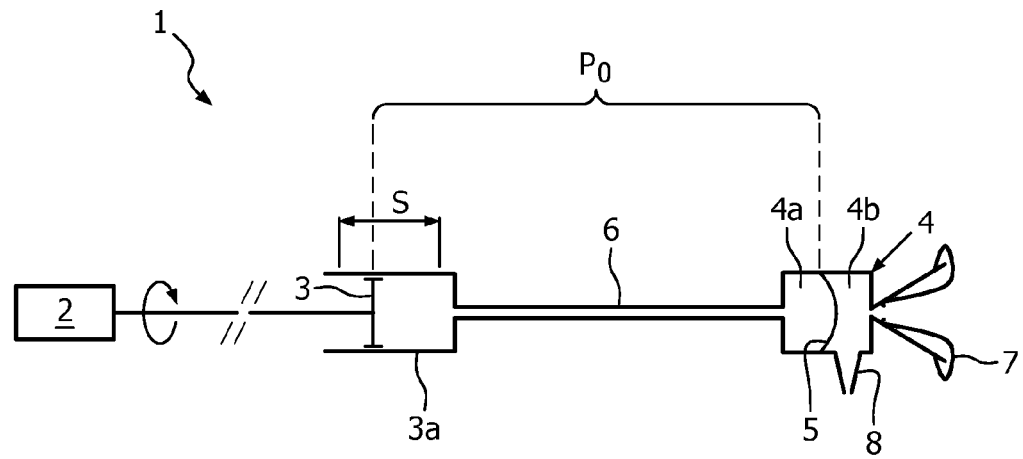
FIG. 1 shows a schematic view of a known breast pump configuration.

Referring now to FIG. 1, a configuration of a known breast pump apparatus 1 is shown schematically and comprises a motor 2 coupled to a piston 3 via a transmission (not shown) which converts rotational motion of the motor 2 into reciprocating motion of the piston 3 such that the piston reciprocates back and forth over stroke distance 'S'. Such a suitable transmission may comprise a cam or eccentric rotational element. The piston 3 is pneumatically coupled to a diaphragm chamber 4 in which a flexible resilient diaphragm 5 separates a closed piston side 4a of the chamber 4 from an open side 4b of the chamber 4. The chamber 3a of the piston 3, the closed side 4a of the diaphragm chamber 4 and connecting duct 6 together form a closed pneumatic system '$P_0$'.

The open side 4b of the chamber 4 is in fluid communication with a funnel portion 7 which is open to outside atmosphere, and the open side 4b of the chamber 4 also includes a valve 8. In use, a feeding bottle (not shown) is attachable to the chamber 4 over the valve 8 to collect milk which is expressed from the mother's breast into the open side 4b of the chamber 4 and which has flowed through the valve 8.

In use, a mother places her breast in the funnel portion 7 which makes an airtight seal therewith, closing the funnel portion 7 from the outside atmosphere. A bottle (not shown) is secured to the chamber 4 over the valve 8 forming a closed space between the open side 4b of the chamber 4 and the bottle. The user then activates the motor 2 to drive the piston 3 back and forth. The reciprocating motion of the piston 3 causes cyclic alternating of pressure within the closed pneumatic system $P_0$, including the closed side 4a of the chamber 4, which causes the diaphragm 5 to deflect back and forth. This, in turn, causes the pressure within the open side 4b of the chamber 4, and thereby, also within the funnel portion 7, to alternate between ambient pressure and a reduced pressure level below atmospheric pressure, thereby stimulating the let-down reflex in the mother's breast causing milk to be expressed into the open side 4b of the chamber 4, from where it flows through the valve 8 into the bottle. The valve 8 is a one-way valve and only allows fluid flow in the direction into the bottle, in order to maximize the pressure difference generated in the open side 4b of the chamber 4 and the funnel portion 7 during operation of the breast pump 1.

It will be appreciated that the alternating pressure changes in the above-described apparatus are caused by the reciprocating piston 3 and that the amplitude of the pressure difference, that is, the size of the pressure difference between maximum and minimum pressure levels in the closed pneumatic system $P_0$, is dictated by the length of the stroke 'S' traveled by the piston 3.

It will also be appreciated that the closed pneumatic system $P_0$ comprises a substantially fixed volume, variable only upon deflection of the resilient diaphragm 5 and movement of the piston 3. Therefore, the only way to be able to vary the pressure depth generated within the closed pneumatic system $P_0$ is to change the distance of the piston stroke 'S'. In order for that to be possible, the motor 2 and transmission (not shown) need to be reversible—i.e. operable in both forwards and backwards directions. This is because a motor which drives a piston, for example by an eccentric cam, in only one direction, would not be capable of allowing the stroke of the piston to be altered. Therefore, the requirement of a reversible motor, and a correspondingly reversible transmission, leads to the inherent disadvantages described above, of a complex system, high cost of manufacture, energy inefficiency leading to increased energy consumption, accelerated wear of the mechanical components and a more expensive motor.

Figure 2:
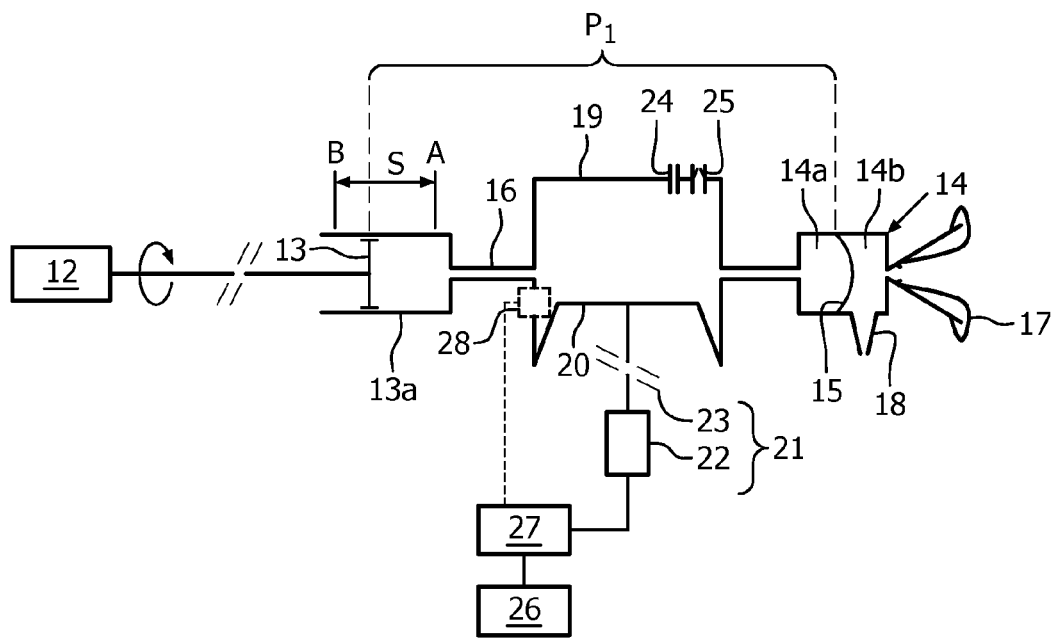
FIG. 2 shows a schematic view of a breast pump configuration of a first embodiment of the invention.

A configuration of a breast pump apparatus 11 of a first embodiment of the invention is shown schematically in FIG. 2 and, as with the known breast pump configuration shown in FIG. 1, comprises a motor 12 coupled to a piston 13 via a transmission (not shown) which converts rotational motion of the motor 12 into reciprocating motion of the piston 13 over stroke distance 'S'. The motor 12 is a unidirectional motor operable to rotate in one direction only. The piston 13 includes a piston chamber 13a which is pneumatically coupled to a closed side 14a of a diaphragm chamber 14 by a connecting duct 16 and, a flexible resilient diaphragm 15 separates the closed piston side 14a of the chamber 14 from an open side 14b.

The open side 14b of the chamber 14 is in fluid communication with a funnel portion 17 which is open to outside atmosphere, and also includes a valve 18 such that, in use, a feeding bottle (not shown) is attachable to the chamber 14 over the valve 18 to collect milk expressed from the mother's breast into the open side 14b of the chamber 14 and which has flowed through the valve 18.

The first embodiment of the invention 11 differs from the known breast pump configuration in that a variable-volume buffer chamber 19 (hereafter referred to as a 'buffer chamber') is disposed in the connecting duct 16 between the piston 13 and the diaphragm chamber 14 such that the chamber 13a of the piston 13, the buffer chamber 19, the closed side 14a of the diaphragm chamber 14 and connecting duct 16 together form a closed pneumatic system '$P_1$'. Furthermore, the buffer chamber 19 has a moveable wall 20 such that the volume of the buffer chamber 19 can be varied. The moveable wall 20 is coupled to an actuator 21 to effect movement of the moveable wall 20. In the embodiment shown, the actuator 21 comprises a second motor 22 connected to the moveable wall 20 via a transmission 23. The transmission 23 may comprise any suitable coupling, for example, a worm gear arrangement may be used. However, the actuator 21 used to move the moveable wall 20 is not limited to this specific arrangement and other mechanisms may be used within the scope of the invention. For example, the moveable wall 20 could be moved by a second piston coupled to a second motor. The buffer chamber 19 also includes a leakage valve 24 and an overpressure valve 25. In use, the leakage valve 24 is configured to allow ambient air to pass into the buffer chamber 19 if the pressure therein falls below a predetermined minimum pressure value. Similarly, the overpressure valve 25 is configured to allow air within the buffer chamber 19 to pass out of the buffer chamber 19 to atmosphere if the pressure therein exceeds a predetermined maximum pressure value, for example, atmospheric pressure.

In this first embodiment of the invention, the 'closed' pneumatic system $P_1$ is defined as 'closed' by virtue of the fact that both the leakage valve 24 and the overpressure valve 25 in the buffer chamber 19 'close' pneumatic system $P_1$ from ambient atmosphere, despite the fact that they are operable, under certain conditions (described below) to allow air into, or to escape from, the pneumatic system, to maintain the pressure range achieved within the closed pneumatic system $P_1$ to remain tuned to the optimum range of values for milk expression.

Operation of the breast pump apparatus 11 of the first embodiment of the invention will now be described. A mother places her breast in the funnel portion 17 making an air-tight seal therewith, and attaches a milk-collecting bottle (not shown) to the diaphragm chamber 14 over the valve 18. The motor 12 is then switched on and the piston 13 is caused to reciprocate back and forth over fixed stroke distance S as the motor 12 rotates in the single direction. The reciprocating motion of the piston 13 causes pressure variations within the closed pneumatic system $P_1$. The closed pneumatic system $P_1$ is at around atmospheric pressure when the piston 13 is at position 'A' within the piston chamber 13a, and the closed pneumatic system $P_1$ is at a negative pressure below atmospheric pressure when the piston 13 is at position 'B' within the piston chamber 13a. The alternating pressure in the closed side 14a of the diaphragm chamber 14 causes the diaphragm 15 to deflect back and forth as the pressure alternates. This in turn creates pressure variations in the open side 14b of the chamber 14, and thereby in the funnel portion 17, which induces the let-down reflex in the mother's breast to cause the breast to express milk. In use, the pressure at the breast may vary within an operating range of around 0 ('base-line' pressure) to −330 mbar pressure, relative to atmospheric pressure, for inducing let-down of milk from the mother's breast. However, the invention is not limited to an apparatus configured to operate within this pressure range and many other pressure ranges are intended within the scope of the invention, such as a smaller or larger pressure range, a range varying between two negative pressures or, a pressure range varying between a negative pressure as a lower pressure range end value and a positive pressure—i.e. a pressure above atmospheric pressure—as an upper pressure range end value.

In the above-described first embodiment of the invention, the speed of movement of the piston 13 determines the frequency of pressure variations within the closed pneumatic system $P_1$ and thereby, within the funnel 17. The 'vacuum depth'—that is, the amplitude of the pressure variation or the magnitude of the negative pressure created within the closed pneumatic system $P_1$—is dependent on the total volume of the closed pneumatic system $P_1$. This is because the magnitude of the negative pressure generated in the closed pneumatic system $P_1$ as the piston 13 moves over stroke distance S from position A to position B is dependent on the proportion of the volume of the piston stroke from position A to position B (the 'swept volume') relative to the total volume of the closed side 14a of the diaphragm chamber 14, the buffer chamber 19 and the connecting duct 16. For example, if the total volume of the closed side 14a of the diaphragm chamber 14, the buffer chamber 19 and the connecting duct 16 was similar to or only slightly larger than the swept volume of the piston 13, then the proportional increase in volume of the closed pneumatic system $P_1$ as the piston moves from position A to position B would be great. Therefore, the density of the air in the closed pneumatic system $P_1$ would greatly reduce (i.e. the number of gas molecules in the closed pneumatic system $P_1$ would be distributed within a relatively much larger total volume), thereby significantly decreasing the pressure in the closed pneumatic system $P_1$. Conversely, if the total volume of the closed side 14a of the diaphragm chamber 14, the buffer chamber 19 and the connecting duct 16 was much greater than the swept volume of the piston 13, then the proportional increase in volume of the closed pneumatic system $P_1$ as the piston moves from position A to position B would be very small. Therefore, the density of the air in the closed pneumatic system $P_1$ would only reduce by a small amount (i.e. the number of gas molecules in the closed pneumatic system $P_1$ would be distributed within only a slightly larger total volume), thereby only slightly decreasing the pressure in the closed pneumatic system $P_1$.

Since the volume of the buffer chamber 19 can be altered by movement of the moveable wall 20 by the actuator 21, the volume of the closed pneumatic system $P_1$ is variable. Therefore, the vacuum depth generated by the apparatus can be varied by controlling the volume of the buffer chamber 19. If the vacuum depth is to be reduced, the volume of the closed pneumatic system $P_1$ is increased by increasing the volume of the buffer chamber 19. This is done by operating the actuator 21 so that the second motor 22 and transmission 23 moves the moveable wall 20 outwards, expanding the buffer chamber 19. The increased volume of the closed pneumatic system $P_1$ means that the pressure variations generated in the closed pneumatic system $P_1$ as the piston 13 moves between the extremes of its range of movement are less pronounced (i.e. since the swept volume of the piston 13 is smaller relative to the total volume of the closed side 14a of the diaphragm chamber 14, the buffer chamber 19 and the connecting duct 16). Therefore, the resilient diaphragm 15 is deflected by a correspondingly lesser amount and so the size of the pressure variations created in the funnel 17 are correspondingly less.

Conversely, if the vacuum depth is to be increased, the volume of the closed pneumatic system $P_1$ is reduced by operating the actuator 21 so that the second motor 22 and transmission 23 move the moveable wall 20 inwards, reducing the buffer chamber 19. The reduced volume of the closed pneumatic system $P_1$ means that the pressure variations generated therein as the piston 13 moves between the extremes of its range of movement are more pronounced (i.e. since the swept volume of the piston 13 is greater relative to the total volume of the closed side 14a of the diaphragm chamber 14, the buffer chamber 19 and the connecting duct 16). Therefore, the resilient diaphragm 15 is deflected by a correspondingly greater degree and so the size of the pressure variations created in the funnel 17 are correspondingly increased.

It will be appreciated that since the pneumatic system $P_1$ is a closed system (i.e. is not freely open to atmosphere), then when the volume of the buffer chamber 19 is increased, the base line pressure in the closed pneumatic system $P_1$ will therefore decrease so that it is then below the desired upper pressure range value (e.g. atmospheric pressure) when the piston 13 is at position 'A'. Correspondingly, the maximum negative pressure achieved when the piston is at position 'B', will be reduced to a level which is lower than the desired lower pressure range value. To prevent this excessive 'negative offset' of the base line pressure, after the buffer chamber 19 volume is increased as described above, when the negative pressure in the closed pneumatic system $P_1$ exceeds a predetermined maximum negative pressure as the piston 13 moves towards position B, the leakage valve 24 is configured to allow ambient air into the buffer chamber 19 such that the pressure in the closed pneumatic system $P_1$ remains at a predetermined negative pressure level when the piston 13 is at position B, and which corresponds to a desired upper pressure range value (e.g. around atmospheric pressure) within the closed pneumatic system $P_1$ when the piston is at position 'A'. However, the leakage valve 24 is configured such that normal operation of the pump does not cause ambient air to pass into the buffer chamber 19 there through, thereby maintaining the pneumatic system $P_1$ as a 'closed' system in normal operation. The leakage valve 24 also comprises an airway restriction configured such that leakage into the buffer chamber 19 occurs in a controlled way.

Conversely, when the volume of the buffer chamber 19 is decreased when a user wishes to increase the generated vacuum depth as described above, since the pneumatic system $P_1$ is a closed system, the base line pressure therein will increase so that it is above the desired upper pressure range value (e.g. atmospheric pressure) when the piston 13 is at position 'A' and, correspondingly, the maximum negative pressure achieved when the piston is in position 'B' will not reach the negative pressure level of the desired lower pressure range value. To prevent this 'positive offset' of the base line pressure, after the buffer chamber 19 volume is decreased as described above, when the pressure in the closed pneumatic system $P_1$ exceeds a predetermined maximum upper pressure range value (e.g. atmospheric pressure) as the piston 13 moves towards position A, the overpressure valve 25 allows air to pass from within the buffer chamber 19 out to atmosphere such that the pressure in the closed pneumatic system $P_1$ remains at the predetermined maximum pressure level (e.g. atmospheric pressure) when the piston is at position 'A'. However, the overpressure valve 25 is configured such that normal operation of the pump does not cause air to escape out of the buffer chamber 19 there through, thereby maintaining the pneumatic system $P_1$ as a 'closed' system in normal operation.

As mentioned above, although the operating range is described as being between 0 (atmospheric pressure) and a predetermined negative pressure, it is intended within the scope of the invention that the operating pressure range may be between a negative pressure at the lower and of the pressure range and a positive pressure (i.e. a pressure above atmospheric pressure) at the upper end of the pressure range. In such an embodiment, the overpressure valve 25 would be configured to only allow air to escape to ambient atmosphere when a pressure above the desired positive pressure is achieved within the closed pneumatic system $P_1$.

Within the scope of the invention, it is intended that the actuator 21 may be automatically controlled, or may be manually set. For example, a user may select one of a number of predetermined operation settings on a user input unit 26 corresponding to a certain vacuum depth, and a controller 27 may control the second motor 22 to position the moveable wall 20 to achieve a corresponding buffer chamber 19 volume to the user-selected setting. Alternatively, the buffer chamber 19 may include a pressure sensor 28 connected to a controller 27 (as shown in broken lines in FIG. 2), and the controller 27 may also control the second motor 22 to position the moveable wall 20 to achieve a corresponding buffer chamber 19 volume in dependence on the detected vacuum depth within the buffer chamber 19 and a desired setting. As a further alternative and simplified embodiment (not shown), the actuator 21 could be entirely manually controlled and simply be a lever or similar device mechanically coupled to the moveable wall 20 wherein a user-selected position of the lever corresponds to one of a number of pre-determined moveable wall 20 positions corresponding to a desired vacuum depth. In such an embodiment, the mechanical coupling between lever and moveable wall could comprise any suitable known arrangement, for example, an eccentric/cam or worm gear.

Figure 3A:
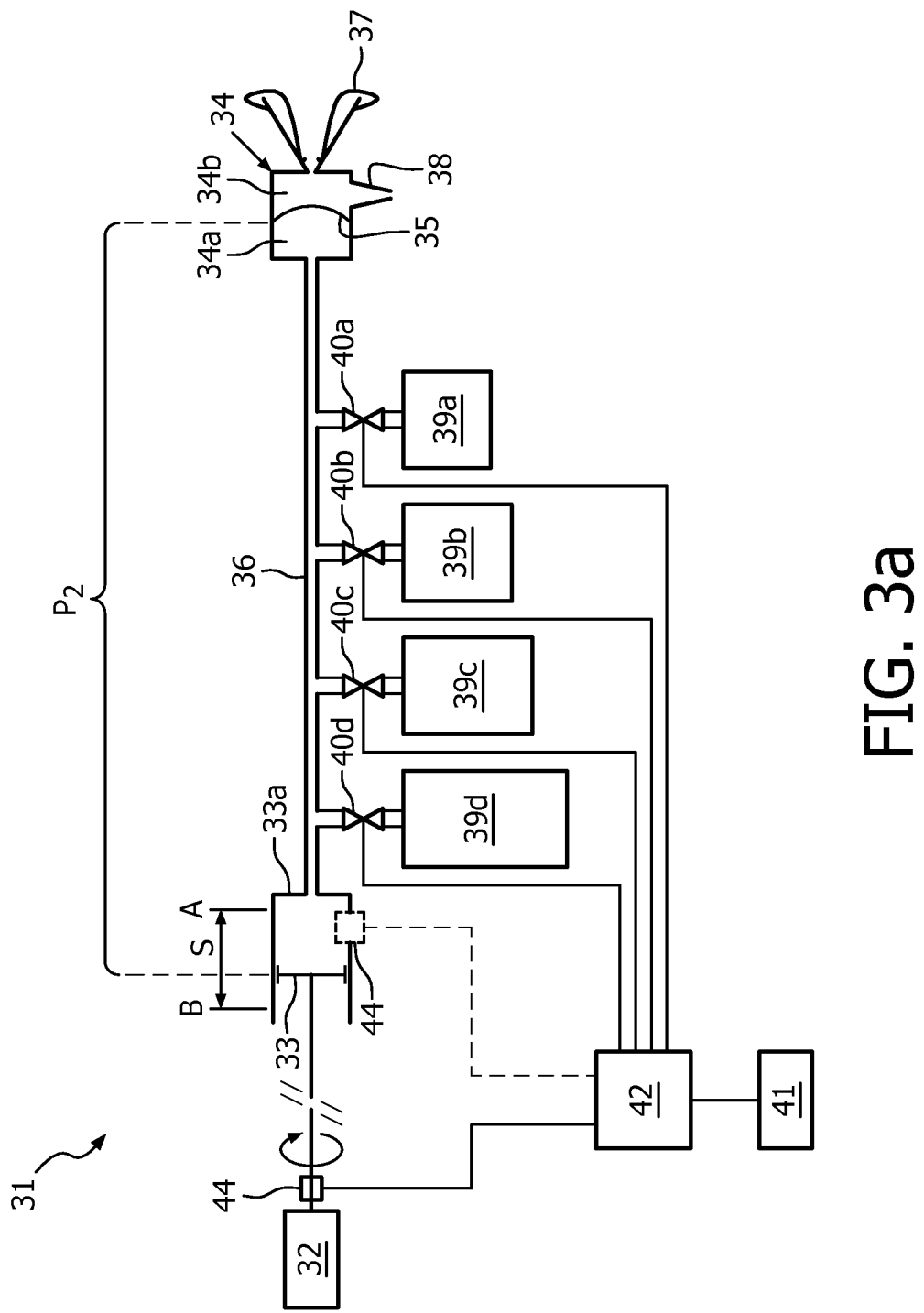
FIGS. 3a-3c show schematic views of three variations of a breast pump configuration of a second embodiment of the invention.
Figure 3B:
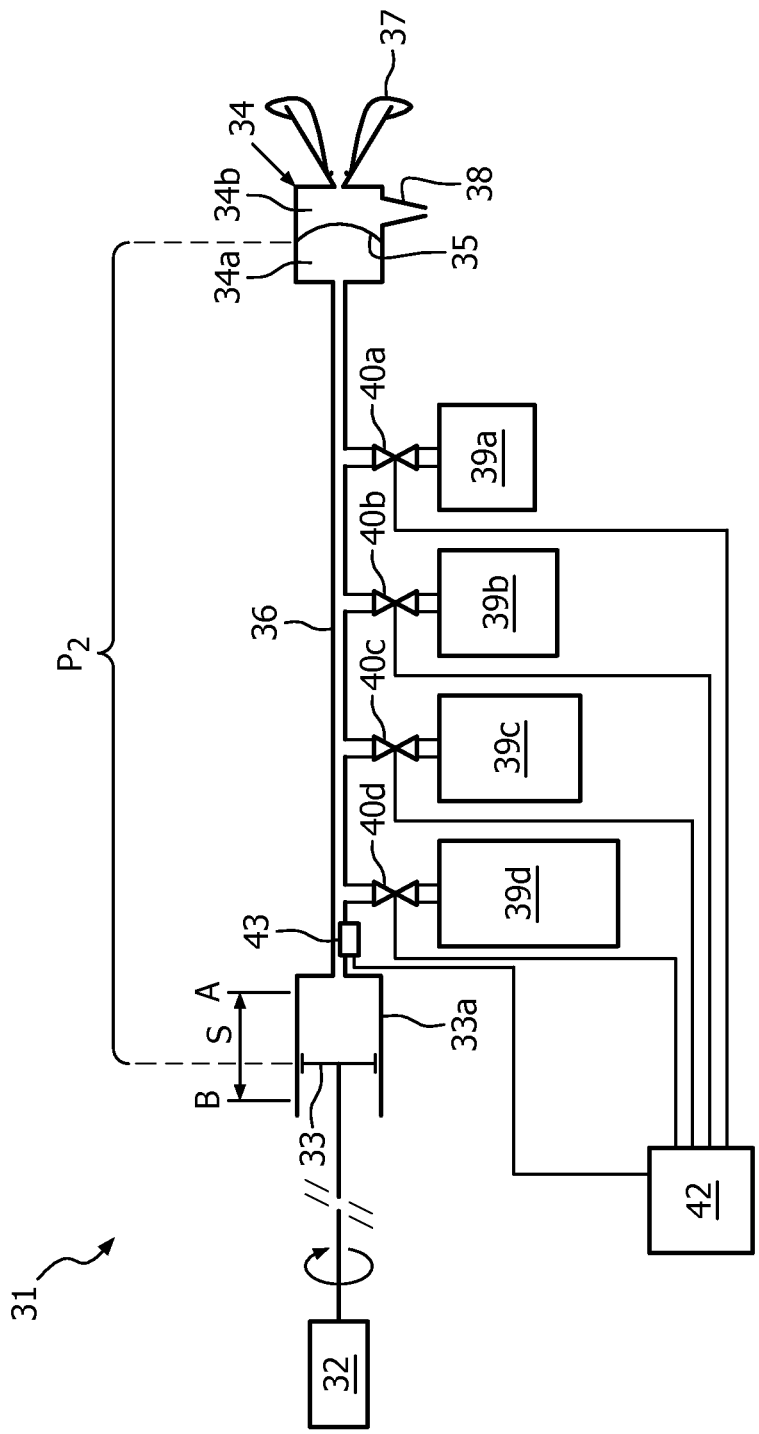
Figure 3C:
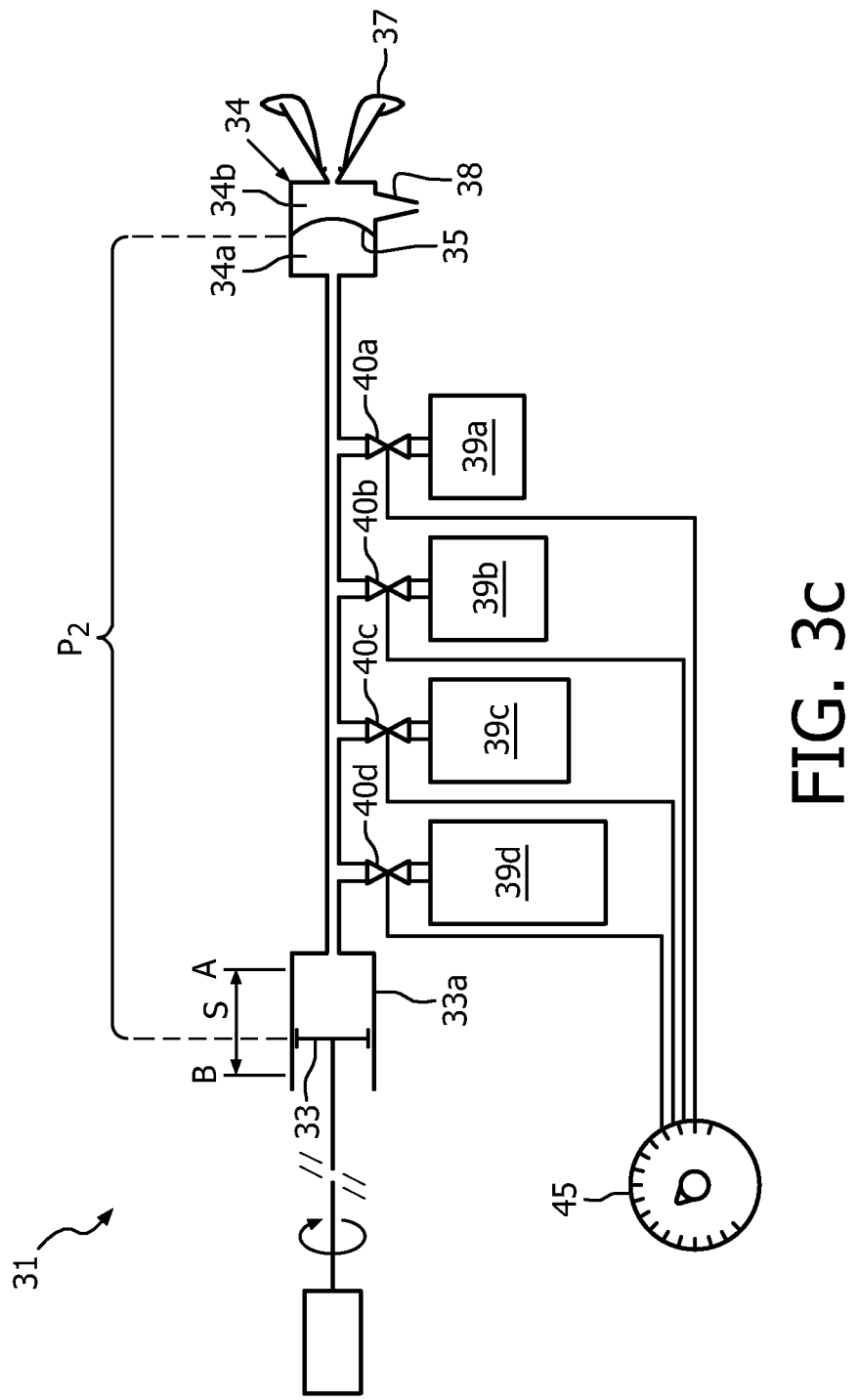

An alternative breast pump apparatus 31 of a second embodiment of the invention is shown schematically as three variations in FIGS. 3a-3c and, as with the breast pump apparatus 11 of the first embodiment of the invention shown in FIG. 2, all variations of the second embodiment comprise a unidirectional motor 32 coupled to a piston 33 via a transmission (not shown) which converts rotational motion of the motor 32 into reciprocating motion of the piston 33 over a fixed stroke distance 'S'. The piston 33 includes a piston chamber 33a which is pneumatically coupled to a closed side 34a of a diaphragm chamber 34 by a connecting duct 36. A flexible resilient diaphragm 35 separates the closed piston side 34a of the chamber 34 from an open side 34b which is in fluid communication with a funnel portion 37 which is open to outside atmosphere. The open side 34b of the chamber 34 also includes a valve 38 to allow collected milk to flow there through into a bottle (not shown) coupled to the chamber 34.

The second embodiment of the invention 31 differs from the first embodiment by the absence of a single variable-volume buffer chamber 19. Instead, the duct 36 includes a plurality of discrete fixed-volume buffer volumes 39a-39d (hereafter referred to as 'buffer volumes') in selective fluid communication with the duct 36. Each buffer volume 39a-d is coupled to the duct by a respective valve 40a-40d such that each buffer volume 39a-d can be independently shut off from being in fluid communication with the duct 36 by shutting the respective valve 40a-d, or be in fluid communication with the duct 36 by having the respective valve 40a-d open.

The chamber 33a of the piston 33, the buffer volumes 39a-d which are in fluid communication with the duct 36, the closed side 34a of the diaphragm chamber 34 and the connecting duct 36 itself, together form a closed pneumatic system '$P_2$'. Each of the valves 40a-d are independently controllable such that any of the buffer volumes 39a-d may be closed off from the closed pneumatic system $P_2$ by shutting the respective valve(s) 40a-d, or may be in fluid communication with the closed pneumatic system $P_2$ by opening the respective valve(s) 40a-d.

The volume of each of the buffer volumes 39a-d is advantageously configured such that each is double the volume of the preceding one. In other words, in terms of arbitrary volume ratio units, the first buffer volume 39a has a volume ratio of 1 unit, the second buffer volume 39b has a volume ratio of 2 units, the third buffer volume 39c has a volume ratio of 4 units and the fourth buffer volume 39d has a volume ratio of 8 units. Using this configuration, the volume of the closed pneumatic system $P_2$ can be varied over a range of 0 volume units to 15 volume units in discrete single volume unit increments. For example, 0 volume units would require all valves 40a-d to be closed, 15 volume units would require all valves 40a-d to be open and, for example, 6 volume units would require the valves 40a, 40d of the first and fourth buffer volumes 39a, 39d (of 1 and 8 volume units respectively) to be closed, and the valves 40b, 40c of the second and third buffer volumes 39b, 39c (of 2 and 4 volume units respectively) to be open.

Operation of the breast pump apparatus 31 of the second embodiment of the invention will now be described. A mother places her breast in the funnel portion 37 making an air-tight seal therewith, and attaches a milk-collecting bottle (not shown) to the diaphragm chamber 34 over the valve 38. The motor 32 is then switched on and the piston 33 is caused to reciprocate back and forth over fixed stroke distance S as the motor 32 rotates in the single direction. The reciprocating motion of the piston 33 causes pressure variations within the closed pneumatic system $P_2$. The closed pneumatic system $P_2$ is at a desired upper pressure range value (for example, around atmospheric pressure) when the piston 33 is at position 'A' within the piston chamber 33a, and the closed pneumatic system $P_2$ is at a desired lower pressure range value of a negative pressure below atmospheric pressure, when the piston 33 is at position 'B' within the piston chamber 33a. The alternating pressure in the closed side 34a of the diaphragm chamber 34 causes the diaphragm 35 to deflect back and forth as the pressure alternates. This in turn creates pressure variations in the open side 34b of the chamber 34, and thereby in the funnel portion 37, which induces the let-down reflex in the mother's breast to cause the breast to express milk. In use, the pressure at the breast may vary within an operating range of around 0 ('base-line' pressure) to −330 mbar pressure, relative to atmospheric pressure, for inducing let-down of milk from the mother's breast. However, the invention is not limited to an apparatus configured to operate within this pressure range and many other pressure ranges are intended within the scope of the invention, such as a smaller or larger pressure range, a range varying between two negative pressures or, a pressure range varying between a negative pressure as a lower pressure range end value and a positive pressure—i.e. a pressure above atmospheric pressure—as an upper pressure range end value.

In the above-described second embodiment of the invention, the speed of movement of the piston 33 determines the frequency of pressure variations within the closed pneumatic system $P_2$ and thereby, within the funnel 37. The 'vacuum depth'—that is, the amplitude of the pressure variation or the magnitude of the negative pressure created within the closed pneumatic system $P_2$—is dependent on the total volume of the closed pneumatic system $P_2$ (for the same reasons explained above in connection with the first embodiment of the invention). Therefore, the vacuum depth generated by the apparatus can be controlled by varying the volume of the closed pneumatic system $P_2$ by controlling the valves 40a-d such that one or more of the buffer volumes 39a-d are either in fluid communication with, or are closed off from, the closed pneumatic system $P_2$.

If the vacuum depth is to be reduced, the volume of the closed pneumatic system $P_2$ is increased by opening one or more of the valves 40a-d so that the respective buffer volume(s) 39a-d are included in the closed pneumatic system $P_2$. The increased volume of the closed pneumatic system $P_2$ proportional to the swept volume of the piston 33 means that the pressure variations generated within the closed pneumatic system $P_2$ as the piston 33 moves between the extremes of its range of movement are less pronounced, for the reasons explained above. Therefore, the resilient diaphragm 35 is deflected by a correspondingly lesser amount and so the size of the pressure variations created in the funnel 37 are correspondingly less.

Conversely, if the vacuum depth is to be increased, the volume of the closed pneumatic system $P_2$ is reduced by closing one or more of the valves 40a-d so that the respective buffer volume(s) 39a-d are closed off from the closed pneumatic system $P_2$. The reduced volume of the closed pneumatic system $P_2$ relative to the swept volume of the piston 33 means that the pressure variations generated within the closed pneumatic system $P_2$ as the piston 33 moves between the extremes of its range of movement result are more pronounced. Therefore, the resilient diaphragm 35 is deflected by a correspondingly greater degree and so the size of the pressure variations created in the funnel 37 are correspondingly increased.

Within the scope of the invention, it is intended that the valves 40a-d may be automatically controlled, or may be manually set. For example, in a first variation of the second embodiment of the invention shown in FIG. 3a, a user may select one of a number of predetermined operation settings on a user input unit 41 corresponding to a certain vacuum depth, and a controller 42 may control each of the valves 40a-d to achieve the desired total volume of the closed pneumatic system $P_2$ by including some of the buffer volume(s) 39a-d within the closed pneumatic system $P_2$ and shutting off other buffer volumes 39a-d from the closed pneumatic system $P_2$ in dependence on the user-selected setting.

In an alternative second variation of the second embodiment of the invention shown in FIG. 3b, the connecting duct 36 (which is always part of the closed pneumatic system $P_2$) may include a pressure sensor 43 connected to the controller 42, and the controller 42 may also control each of the valves 40a-d to achieve a total closed pneumatic system $P_2$ volume in dependence on the detected vacuum depth within the closed pneumatic system $P_2$ and a desired predetermined setting held within the controller 42.

As a further alternative, and simplified, third variation of the second embodiment of the invention shown in FIG. 3c, the valves 40a-d could be entirely manually controlled by a manual actuator 45 wherein a user-selected actuator position corresponds to one of a number of pre-determined valve 40a-d opening/closing configurations to achieve a desired vacuum depth.

In order to prevent abrupt changes in the vacuum level in the above-described second embodiment of the invention, it would be desirable that the opening or closing of the valves 40a-d of the buffer volumes 39a-d would be synchronized to the point of the piston stroke S at which the pressure in the closed pneumatic system $P_2$ is at the desired upper pressure range value (e.g. zero/atmospheric pressure). This would advantageously be at the extreme inward point of the piston movement indicated at position 'A'. Therefore, if a valve 40a-d is closed at this timing, the pressure within the buffer volume 39a-d which is then sealed from the rest of the closed pneumatic system $P_2$ would be at the desired upper pressure range value (e.g. zero/atmospheric pressure) and as the respective valve 40a-d is closed, the pressure within the sealed buffer volume 39a-d would remain at this level until the valve 40a-d is opened again. Furthermore, if, as mentioned above, the valve(s) 40a-d are only opened in synchronization when the piston 33 is at a position such that the pressure in the closed pneumatic system $P_2$ is at the desired upper pressure range value (e.g. zero/atmospheric pressure), the opening of the valve 40a-d to bring the respective buffer volume 39a-d into fluid communication with the rest of the closed pneumatic system $P_2$ again, would not cause any pressure fluctuation as both the buffer volume 39a-d and the closed pneumatic system $P_2$ would be at the same pressure at that moment (i.e. the desired upper pressure range value, for example, zero/atmospheric pressure). This synchronization of valve 40a-d opening could be achieved using a pressure sensor 43 located in the duct 36, as shown in FIG. 3b, coupled to the controller 42 which is connected to the valves 40a-d and which is configured only to open/close the valves 40a-d when the sensed pressure in the duct 36 is at the desired upper pressure range value (e.g. zero/atmospheric pressure). Alternatively, the same controller 42 which is connected to the valves 40a-d and configured to open/close them, could be coupled to an alternative sensor 44 mounted on the motor 32 axle (as shown in solid lines in FIG. 3a) or on the piston 33 (as shown in dashed lines in FIG. 3a) such that the valves 40a-d are only opened/closed when the motor axle position or the piston stroke position corresponds to a point at which the pressure in the closed pneumatic system $P_2$ is at the desired upper pressure range value (e.g. zero/atmospheric pressure).

Although the respective volumes of each of the buffer volumes 39a-d are described in the above exemplary second embodiment of the invention as being of increasing doubling volume ratios, the invention is not limited to this configuration, and the plurality of buffer volumes 39a-d may be of different relative volume ratios, for example, they could all be the same, or they could differ in alternative relative volume ratios to each other than that described above.

Figure 4:
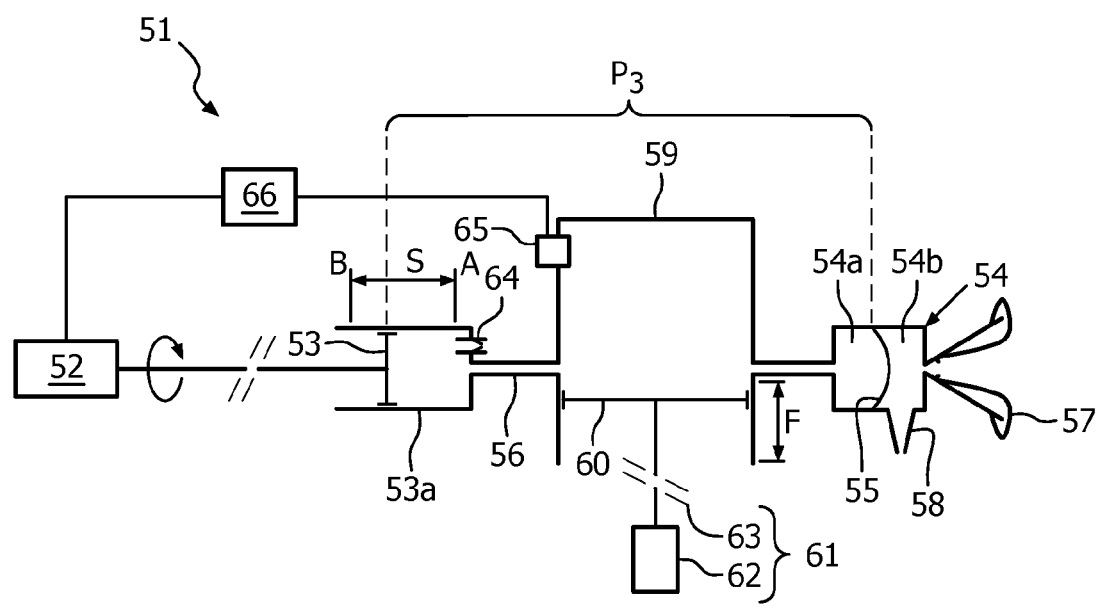
FIG. 4 shows a schematic view of a breast pump configuration of a third embodiment of the invention.

A further alternative breast pump configuration 51 of a third embodiment of the invention is shown schematically in FIG. 4 and, as with the breast pump configuration 11 of the first embodiment of the invention shown in FIG. 2, comprises a unidirectional motor 52 coupled to a first piston 53 via a transmission (not shown) which converts rotational motion of the motor 52 into reciprocating motion of the first piston 53 over a fixed stroke distance 'S'. The first piston 53 includes a piston chamber 53a which is pneumatically coupled to a closed side 54a of a diaphragm chamber 54 by a connecting duct 56 and, a flexible resilient diaphragm 55 separates the closed piston side 54a of the chamber 54 from an open side 54b. An intermediate variable-volume buffer chamber 59 (hereafter referred to as a 'buffer chamber') is disposed between the first piston 53 and the diaphragm chamber 54 in the connecting duct 56 such that the chamber 53a of the first piston 53, the buffer chamber 59, the closed side 54a of the diaphragm chamber 54 and connecting duct 56 together form a closed pneumatic system '$P_3$'.

The open side 54b of the diaphragm chamber 54 is in fluid communication with a funnel portion 57 which is open to outside atmosphere, and also includes a valve 58 such that, in use, a feeding bottle (not shown) is attachable to the chamber 54 over the valve 58 to collect milk expressed from the mother's breast into the open side 54b of the chamber 54 and which has flowed through the valve 58.

The third embodiment of the invention 51 differs from the breast pump configuration of the first embodiment of the invention in that the buffer chamber 59 comprises a piston chamber having a second piston 60 reciprocating moveable therein such that the volume of the buffer chamber 59 can be varied. The second piston 60 is coupled to an actuator 61 to effect movement thereof. In the embodiment shown, the actuator 61 comprises a second motor 62 connected to the second piston 60 by a transmission 63. The transmission 63 may comprise any suitable coupling to translate rotational drive of the second motor 62 into reciprocating movement of the second piston 60, such as, for example, a cam or eccentric member. The second piston 60 moves over a fixed stroke distance F within the buffer chamber 59. In addition to the above, the first piston chamber 53a includes a one way outlet valve 64 which is operable to allow air out of the first piston chamber 53a but prevents air from passing from ambient atmosphere into the first piston chamber 53a.

Operation of the breast pump apparatus 51 of the third embodiment of the invention will now be described. A mother places her breast in the funnel portion 57 making an air-tight seal therewith, and attaches a milk-collecting bottle (not shown) to the diaphragm chamber 54 over the valve 58. The motor 52 is then switched on and the first piston 53 is caused to reciprocate back and forth over fixed stroke distance S as the motor 52 rotates in the single direction.

The configuration of the motor 52 and first piston 53 of the third embodiment 51 of the invention differs from the corresponding configuration of the first and second embodiments of the invention described above, in that the reciprocating motion of the first piston 53 does not cause the cyclic varying pressure fluctuations within the closed pneumatic system $P_3$. Instead, the first piston 53 reciprocates back and forth much faster than the rate at which pressure fluctuation cycles are required at the breast. As the first piston moves quickly from its fully extended position 'B' to its fully refracted position 'A', the brief localized increase in pressure causes the outlet valve 64 to open and air within the first piston chamber 53a to pass out thereof though the outlet valve 64. Then, as the first piston 53 travels in the opposite direction, the outlet valve 64 is forced shut and so a vacuum is generated in the first piston chamber 53a and thereby also in the closed pneumatic system $P_3$. The above process is then repeated such that the quick repeated reciprocating action of the first piston 53 generates a substantially constant base-level negative pressure within the closed pneumatic system $P_3$. The speed at which the first piston 53 reciprocates determines the constant 'vacuum depth' of the base-level negative pressure generated within the closed pneumatic system $P_3$.

Given the above constant base level negative pressure is created as described above within the closed pneumatic system $P_3$, alternating pressure cycles are then generated by varying the volume of the buffer chamber 59 by movement of the second piston 60. Therefore, the second motor 62 is powered to drive the second piston 60 in a reciprocating manner and the volume of the closed pneumatic system $P_3$ is increased and decreased as the second piston 60 reciprocates between the extremes of its range of motion. Therefore, the frequency of the changing vacuum/pressure cycles within the closed pneumatic system $P_3$ is dictated by the speed at which the second piston 60 reciprocates. As the second piston 60 is only driven to determine the frequency of the pressure fluctuations and not the magnitude/amplitude of the pressure fluctuations, the second motor 62 is a unidirectional motor and is not required to be operable in two directions, and the stroke F of the second piston 60 is constant. Therefore the disadvantages of two-directional motors and transmissions described above are avoided.

As with the first and second embodiments of the invention described above, the alternating vacuum level generated in the closed side 54a of the diaphragm chamber 54 causes the diaphragm 55 to deflect back and forth as the pressure alternates. This in turn creates pressure variations in the open side 54b of the chamber 54, and thereby in the funnel portion 57, which induces the let-down reflex in the mother's breast to cause the breast to express milk. In use, the pressure at the breast may vary within an operating range of around 0 ('baseline' pressure) to −330 mbar pressure, relative to atmospheric pressure, for inducing let-down of milk from the mother's breast. However, the invention is not limited to an apparatus configured to operate within this pressure range and many other pressure ranges are intended within the scope of the invention, such as a smaller or larger pressure range, a range varying between two negative pressures or, a pressure range varying between a negative pressure as a lower pressure range end value and a positive pressure—i.e. a pressure above atmospheric pressure—as an upper pressure range end value.

It will be appreciated from the above that the maximum and minimum pressures achieved within the closed pneumatic system $P_3$ are determined by the base-level negative pressure depth generated by the first piston 53. Therefore, in order that the pressure within the closed pneumatic system $P_3$ varies within the desired range over the cycles, the frequency of which is dictated by the second piston 60, a pressure sensor 65 is provided in the buffer volume 59 and is connected to a controller 66. The controller 66 is also connected to the first motor 52 and controls the speed of the first motor 52 in dependence upon the sensed pressure levels within the buffer volume 59. For example, if the sensed negative pressure range achieved within the buffer volume 59 (and thereby within the closed pneumatic system $P_3$ as a whole) is too much of a negative pressure, the controller 66 controls the speed of the first motor 52 to be reduced, thereby reducing the base-level negative pressure depth within the closed pneumatic system $P_3$ and therefore, also reducing the negative pressure depth achieved over the range of the alternating pressure cycles within the closed pneumatic system $P_3$.

Conversely, if the sensed negative pressure range achieved within the buffer volume 59 is insufficient, the controller 66 controls the speed of the first motor 52 to be increased, thereby increasing the base-level negative pressure depth within the closed pneumatic system $P_3$ and therefore, also increasing the negative pressure depth achieved over the range of the alternating pressure cycles within the closed pneumatic system $P_3$.

Although in the above-described third embodiment of the invention, the pressure sensor 65 is located in the buffer chamber 59 to detect the pressure within the closed pneumatic system $P_3$, the sensor could alternatively be located within the open side 54b of the diaphragm chamber 54 to detect the pressure variations resulting from the deflection of the diaphragm 55, and control the speed of the first motor 52 in dependence on whether the negative pressure variation in the open side 54b of the diaphragm chamber 54 meets predetermined criteria.

All of the exemplary embodiments of the invention described above comprise a diaphragm chamber which includes a resilient diaphragm separating the chamber into two sides, one closed side in fluid communication with the vacuum pump and the buffer chamber/volume, and an open side in fluid communication with the breast-receiving funnel portion. In such embodiments, the funnel portion is thereby not in fluid communication with the buffer chamber/volume, and the closed pneumatic system only includes the closed side of the diaphragm chamber, the buffer chamber/volume, the vacuum pump and the connecting duct. However, it is intended within the scope of the invention that the breast pump apparatus may not include a diaphragm chamber with a diaphragm separating the breast-receiving funnel portion from the buffer chamber/volume and the vacuum pump. In such (unillustrated) alternative embodiments within the scope of the invention, the funnel portion may be coupled by the duct in direct fluid communication with the buffer chamber/volume. Alternatively, an intermediate chamber may be provided between the duct and the funnel portion, similar to the diaphragm chamber without a diaphragm therein, in order to facilitate collection of expressed milk, but the funnel would still be in fluid communication with the buffer chamber/volume and vacuum pump. Therefore, the negative pressure generated by the vacuum pump and controlled by the buffer chamber/volume would act directly on the breast at the funnel portion, without being transmitted to a separate closed space by the resilient diaphragm. In such embodiments, the closed pneumatic system would be formed when the mother places her breast in the funnel portion, thereby closing off that opening, and the closed pneumatic system would comprise the vacuum pump, duct, buffer chamber/volume, funnel portion and, if provided, intermediate chamber.

In the specific exemplary embodiments of the invention described above, the vacuum pump is shown and described as a reciprocating piston pump. However, as mentioned above, other types of pump may be employed within the scope of the invention as a vacuum source. For example, the vacuum pump could comprise a membrane pump, which comprises a motor connected to a small piston, the piston coupled to a membrane. A pump chamber the other side of the piston is closed by the membrane and is connected to the variable buffer volume via a first valve. Running the motor operates the piston to deflect the membrane in a first direction to increase the volume of the pump chamber and thereby extract air from the attached buffer volume through the first valve. The piston then deflects the membrane in the opposite direction, reducing the volume of the pump chamber. This closes the first valve but opens a second valve in the pump chamber to allow the air to be expelled to ambient atmosphere. This process is repeated as the piston reciprocates, thus creating a vacuum in the attached buffer volume.

Another type of pump which may be used within the scope of the invention is a disc pump. This is similar to the membrane pump described above, but instead of being driven by a motor and piston, the driving actuator comprises an ultrasonic disc driven by piezoelectric actuators.

It will be appreciated that all embodiments of the invention comprise a vacuum pump to create a negative pressure within the breast pump apparatus, but that control over the negative pressure fluctuations experienced at the breast can be achieved by varying the volume of the buffer volume, independently of the vacuum pump. This functionality allows the vacuum control function to be achieved in a breast pump apparatus with a simpler, more robust and less expensive design.

Throughout the description, the term 'vacuum' is used to describe any negative pressure—namely, a pressure below atmospheric pressure—and does not necessarily mean 'vacuum' as a total absence of gas molecules in a given space—i.e. it does not necessarily mean an absolute vacuum. Likewise, the term 'vacuum pump' is used to describe a pump device capable of producing a negative pressure in a closed system, not necessarily a pump operable to entirely evacuate a closed system to create an absolute vacuum.

Although claims have been formulated in this application to particular combinations of features, it should be understood that the scope of the disclosure of the present invention also includes any novel features or any novel combination of features disclosed herein either explicitly or implicitly or any generalization thereof, whether or not it relates to the same invention as presently claimed in any claim and whether or not it mitigates any or all of the same technical problems as does the present invention. The applicants hereby give notice that new claims may be formulated to such features and/or combinations of such features during the prosecution of the present application or of any further application derived there from.

The invention claimed is:

1. A breast pump apparatus comprising:
   a vacuum pump operable to generate at least a negative pressure in a closed volume;
   a breast-receiving portion configured to receive a woman's breast from which milk is to be expressed; and
   a buffer volume;
   wherein the buffer volume is coupled to the vacuum pump and to the breast-receiving portion such that, in use, the vacuum pump is operable to generate at least the negative pressure in the buffer volume and at the breast-receiving portion;
   wherein the vacuum pump generates and releases the negative pressure cyclically, and
   wherein the buffer volume is variable such that, in use the amplitude of the negative pressure generated at the breast-receiving portion can be controlled by varying the buffer volume and wherein the buffer volume is held constant during cycles of the vacuum pump.

2. A breast pump apparatus according to claim 1 wherein the buffer volume comprises a variable-volume chamber.

3. A breast pump apparatus according to claim 2 wherein the variable volume chamber comprises a piston housing and a piston within the piston housing, and wherein the volume of the buffer volume can be varied by moving the piston with the piston housing.

4. A breast pump apparatus according to claim 3 wherein the pump is configured to generate a substantially constant negative pressure and the piston is configured to reciprocate within the piston housing to cyclically vary the pressure at the breast receiving portion.

5. A breast pump apparatus according to claim 2 wherein the variable volume chamber comprises a housing having a moveable wall portion, and wherein the volume of the buffer volume can be varied by moving the moveable wall portion relative to the housing.

6. A breast pump apparatus according to claim 5 wherein the vacuum pump is configured to cyclically generate varying negative pressure at the breast-receiving portion and the moveable wall of the variable volume chamber is controllable to determine the amplitude of the negative pressure variations at the breast-receiving portion.

7. A breast pump apparatus according to claim 1 wherein the buffer volume comprises a plurality of fixed volume chambers, each in fluid communication with the pump via a respective valve, and wherein the volume of the buffer volume in fluid communication with the pump can be varied by selectively opening or closing each valve independently of each other valve so that the fixed volume chambers can selectively be closed off from, or in fluid communication with, the pump.

8. A breast pump apparatus according to claim 7 wherein each of the fixed volume chambers has a different volume to each of the other of the fixed volume chambers.

9. A breast pump apparatus according to claim 8 wherein the pump is configured to cyclically generate varying negative pressure at the breast-receiving portion and the valves of the fixed volume chambers are independently controllable to determine the amplitude of the negative pressure variations at the breast-receiving portion.

10. A breast pump apparatus according to claim 1, further comprising a pressure sensor in fluid communication with the buffer volume, a controller coupled to the pressure sensor and to the buffer volume, and wherein the volume of the buffer volume can be varied in dependence on a sensed pressure.

11. A breast pump apparatus according to claim 1, further comprising a motor and wherein the pump comprises a reciprocating piston or membrane pump driven by the motor.

12. A breast pump apparatus according to claim 1, further comprising a diaphragm chamber and a flexible diaphragm mounted therein separating the diaphragm chamber into a closed side which is in fluid communication with the pump and the buffer volume and, an open side, wherein the breast-receiving portion is coupled in fluid communication with the open side of the diaphragm chamber such that pressure variations generated in the closed side cause the resilient diaphragm to deflect and thereby transmit the pressure variations to the open side and to the breast-receiving portion.

13. A method of controlling a breast pump apparatus which comprises a vacuum pump, a breast-receiving portion configured to receiving a woman's breast from which milk is to be expressed, and, a variable buffer volume coupled to the vacuum pump and to the breast-receiving portion;

the method comprising operating the vacuum pump to generate at least a negative pressure in the buffer volume and at the breast-receiving portion; and controlling the amplitude of the negative pressure generated at the breast-receiving portion, by controlling the variable buffer volume, wherein the vacuum pump generates and releases the negative pressure cyclically, and wherein the buffer volume is held constant during cycles of the vacuum pump.

14. A method according to claim 13 wherein the buffer volume comprises a variable-volume chamber and wherein the pressure at the breast-receiving portion is varied by controlling the volume of the variable-volume chamber.

15. A method according to claim 13 wherein the buffer volume comprises a plurality of fixed volume chambers in fluid communication with the vacuum pump via a respective valve, and wherein the method further comprises varying the total volume of the buffer volume in fluid communication with the vacuum pump by selectively opening or closing each valve independently of each other valve so that each of the fixed volume chambers is selectively closed off from or in fluid communication with, the vacuum pump.

* * * * *